United States Patent [19]

Crane

[11] Patent Number: 5,489,506

[45] Date of Patent: Feb. 6, 1996

[54] DIELECTROPHORETIC CELL STREAM SORTER

[75] Inventor: Stuart Crane, Grosse Pointe Park, Mich.

[73] Assignee: Biolife Systems, Inc., Farmington Hills, Mich.

[21] Appl. No.: 391,403

[22] Filed: Feb. 16, 1995

Related U.S. Application Data

[63] Continuation of Ser. No. 966,878, Oct. 26, 1992, abandoned.

[51] Int. Cl.[6] .................................................. G01N 33/483
[52] U.S. Cl. .......................... 435/2; 436/63; 435/7.24; 435/29; 209/3.1; 209/552; 209/571; 209/127.4; 356/72; 356/73; 324/71.4; 361/226; 250/461.2
[58] Field of Search .......................... 436/63; 435/2, 435/7.24, 29; 356/72, 73; 209/3.1, 552, 571, 127.4; 324/71.4; 361/226; 250/461.2

[56] References Cited

U.S. PATENT DOCUMENTS

| | | | |
|---|---|---|---|
| 4,175,662 | 11/1979 | Zöld | 209/552 |
| 4,300,310 | 11/1981 | Galbraith | 435/172.2 |
| 4,326,934 | 4/1982 | Pohl | 204/180 R |
| 4,347,935 | 9/1982 | Merrill | 209/3.2 |
| 4,440,638 | 4/1984 | Judy et al. | 210/198.2 |
| 4,510,244 | 4/1985 | Parks et al. | 435/172.2 |
| 4,515,274 | 5/1985 | Hollinger et al. | 209/3.1 |
| 4,519,506 | 5/1985 | Spaanderman | 209/592 |
| 4,520,456 | 5/1985 | Miranker et al. | 395/800 |
| 4,557,014 | 12/1985 | Vogt | 452/151 |
| 4,599,304 | 7/1986 | Lanier et al. | 435/7.24 |
| 4,607,007 | 8/1986 | Lanier et al. | 435/7.24 |
| 4,667,830 | 5/1987 | Nozaki, Jr. et al. | 209/3.1 |
| 4,675,286 | 6/1987 | Calenoff | 435/7.24 |
| 4,677,061 | 6/1987 | Rose et al. | 435/7.24 |
| 4,816,395 | 3/1989 | Hancock et al. | 435/29 |
| 4,818,679 | 4/1989 | Chasin et al. | 435/6 |
| 4,824,775 | 4/1989 | Dattagupta et al. | 435/4 |
| 4,936,465 | 6/1990 | Zold | 209/3.1 |
| 4,954,715 | 9/1990 | Zold | 250/461.1 |

Primary Examiner—James C. Housel
Assistant Examiner—Rachel Heather Freed
Attorney, Agent, or Firm—Groh, Sprinkle, Patmore, Anderson & Citkowski Gifford, Krass

[57] ABSTRACT

A method and apparatus for continuously sorting living cells from a mixture of many unlike cells to obtain separate populations of like cells. The invention comprises cell and fluid intake ports, a cell deflection chamber, and a series of output vacuum pumps attached to a like number of collection reservoirs. The cell intake section is a two-stage system that first mixes the incoming cells with a deionized, buffered, processing medium then sheathes the output stream with a centering carrier fluid. An expansion chamber contains one or more electrodes connected to one or more RF generators that act upon the passing cells so that they are fanned out within the expansion chamber according to their size, physical construction, chemical composition and electronic properties. Vacuum pumps draw the fluids through the system and deposit the sorted cells in separate reservoirs.

6 Claims, 4 Drawing Sheets

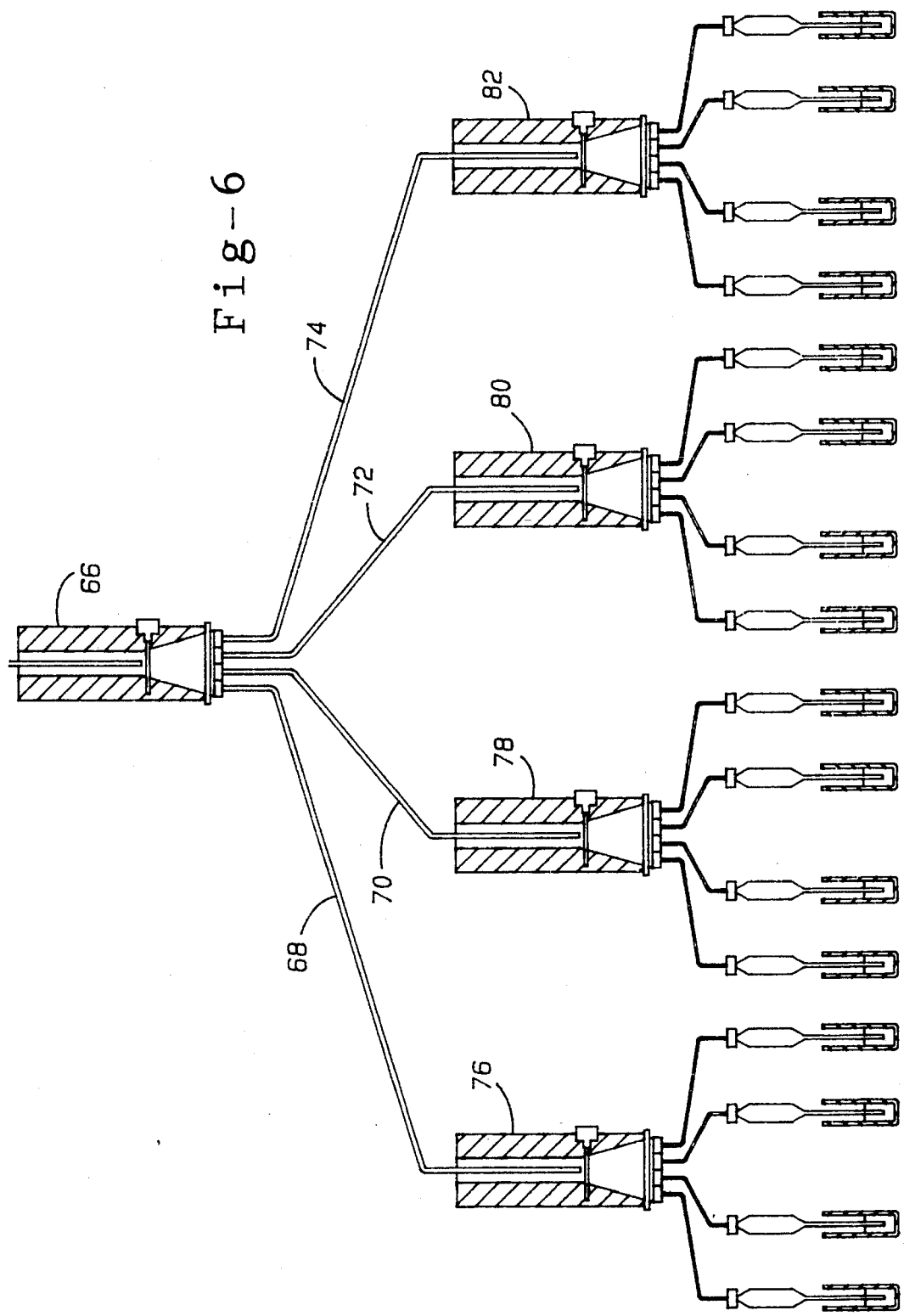

DIELECTROPHORETIC CELL STREAM SORTER

This is a continuation of application Ser. No. 07/966,878 filed on Oct. 26, 1992, now abandoned.

BACKGROUND OF THE INVENTION

I. Field of the Invention

The present invention relates to a method and apparatus for splitting a continuous stream of heterogeneous living cells into numerous separate vessels each containing a single type of homogeneous cells. More particularly, the present invention relates to the use of electronic, high frequency fields combined with gravity pumps to cleanly separate living cells.

II. Description of the Relevant Art

An important facet in the treatment and prevention of disease is the identification, isolation and analysis of cells and cellular material. Once isolated, individual cells can be investigated to better understand cell function and transformation. Clean separation of discrete cell types from a highly mixed heterogeneous population would allow for the removal of one cell type from that population, for example, leukemia cells from blood. Better separation could improve the physician's analysis of blood samples.

While investigation of living cells is undertaken by other means, it is the limitations of cell sorting that has limited cell testing, research and analysis. This is a considerable obstacle, since the subjects under investigation have normally been hard to obtain in adequate quantity and quality. Scientists are still plagued with the inability to cleanly obtain identifiable cell lines in good condition, such as non-toxic, homogeneous, viable forms from a mixture of similar cells for study or removal.

In the mid-1970's a technique called fluorescence-activated cell sorting was developed employing fluorescent dyes (specifically, fluorescein, a dye that glows an intense greenish-blue fluorescence by reflected light, while being reddish-orange by transmitted light). By this method, the dye is mixed with the cells and adheres selectively to different surface features of a particular cell type. The stream of mixed cells, dyed and suspended in fluid, is passed through a rapidly vibrating nozzle that breaks the fluid into small droplets containing individual cells. The stream of individual droplets then passes through a laser beam thus exciting the fluorescein fixed to the cells. By converting the glow to an electrical signal, the fluorescent cells receive a negative charge, the non-fluorescent cells receive a positive charge, and other droplets remain uncharged.

The mixture of charged and uncharged droplets is then passed through an electric field that causes positively charged cells to migrate toward a negative deflection plate, the negatively charged cells to migrate to a positively charged deflection plate, and the uncharged cells to pass between the plates. Collectors are provided to gather groups of separated cells.

While fluorescence-activated cell sorting represented a substantial move in the right direction in providing a method of isolating certain types of cancerous cells and cells of the immune system, this method has several disadvantages. While having relatively low toxicity, fluorescein is still toxic. Its toxicity notwithstanding, the inclusion of a dye in the process adds both another layer of work for the technician and another element to the product. In addition, many different cells respond similarly to the dye and are therefore not separable by this method. Further, all cells are not able to withstand the intense laser light or the high voltages (2,000+ volts) necessary for this type of sorting. Because cell viability is the essential requirement of virtually all cellular investigation and therapy, this sorting method is limited by the low survival rate of the cells.

In the early 1980's, several methods were developed that claimed to avoid the fatal results of the fluorescence-activated cell sorting method. An example is seen in U.S. Pat. No. 4,326,934, issued to Herbert A Pohl for "Continuous Dielectrophoretic Cell Classification Method". The method of this patent takes advantage of the principle of dielectrophoresis which is employed in, for example, the petroleum industry where it is used to extract sulphur from crude oil.

As applied to biological systems, the process disclosed in the patent to Pohl subjected cells to a non-uniform electric field between two electrodes. Dielectrophoresis is said to cause cells to separate from one another and then be collected in two separate chambers. The shortcomings of this method were that Pohl had no means to make a final physical separation of the stream without turbulence and subsequent remixing of the elements before they entered the final reservoirs. In actuality, he never achieved this separation. The patent does not address the necessity of carrying the cells in a deionized solution, nor the necessity of using a high frequency alternating field. Finally, the shape of the Pohl tube does not allow for the spreading of the cells in the field because of its uniform configuration throughout that eliminates the adjustability and fine tuning required for quality sorting.

Accordingly, a method of sorting cells with a high degree of differentiation and viability is still wanting. This need has not been met by earlier efforts to overcome the common problems in sorting cells.

SUMMARY OF THE PRESENT INVENTION

The present invention overcomes the shortcomings of known cell sorting technology by providing a method and apparatus for sorting cells in high volume, at rapid speed, with high reliability, with excellent viability, all at a relatively low cost.

When ionized cells are placed in an electronic field, the cell's internal ions migrate toward the opposite charged electrode and the normally non-polar cell (as a unit) becomes, in time, an electronic dipole. If the field charge is reversed as the ions within the cell attempt to migrate toward the opposite field charge, the cell's internal ions must also change direction. The rate at which the ions can make the altering migration within the cell varies with every attribute of the cell itself, such as the cell's size, shape, chemical and physical construction, and electronic conductivity. These attributes give each type of cell a unique electronic fingerprint. The ion migration of some cells may be completed in the time allowed at the particular electronic alternating radio frequency and the dipoled cell migrates rapidly toward the small pole of the non-uniform field (see Dielectrophoresis, H. A. Pohl, Cambridge University Press, 1978, pp. 432–440). Such a cell remains a strong dipole because it is synchronized with the field. The ions of other cells are not able to make the trip in the time allowed and will be electronically "confused" and will become partially polarized or remain essentially non-polar at that particular frequency. Thus some cells will not migrate at all, while others fall into various degrees of dipolarity and migrate at various rates in the RF field.

According to the present invention, the cells to be sorted are introduced into the sorting system in two stages. In the first stage, the cells in growing medium are introduced into a highly deionized, buffered medium. This solution is then passed through the second stage where a sheathing carrier fluid surrounds the cell stream. This coaxial stream then passes into the sorting chamber.

The chamber may either be a single chamber design, or may be a multiple "stacked" chamber. This latter construction is useful where a particularly large number of cells are to be sorted simultaneously.

The chamber includes an expansion region. In the expansion chamber, cells are subjected to a sorting RF field. The RF field can be adjusted in both frequency and strength according to need. In addition, several RF field generator electrodes may be employed to more discretely manipulate the cells. Further fine tuning of the system may be achieved by strategic spacing of electrodes from various field generators set to different frequencies and amplitudes.

The expansion chamber includes a narrowed and restrictive entryway and terminates in a wider exit. This fan-shaped construction accommodates the shape of the fanned-out mixture resulting from exposure to one or more of the RF fields small electrodes (a fine platinum wire laid in the direction of the flow) on one side of the chamber and opposed to a wide ground electrode on the opposite side. This arrangement provides for a high nonuniformness of the field. The passing concentrated cell stream is spread apart (fanned) so that the "synchronized" cells are directed toward one end of the chamber (the small electrode) while the less "synchronized" cells are in various positions in the outbound stream.

The now-sorted cells exit the deflection chamber in fluid lines that carry the cells to an array of gravity vacuum pumps. An important feature of the present invention, the gravity vacuum pumps draw the fluid from the sorting chamber and deposit the sorted cells into the nearest individual cell recovery reservoirs with the complete absence of turbulence. Because the mixture is drawn through the system rather than being pushed, physical separation is markedly improved in both the number of cells recovered and the accuracy of sorting. This is possible because the drawing system eliminates use of the "doctor's knife" where turbulence is always created just before the point of stream separation, the common problem of all known systems.

The system may be used in a cascading arrangement whereby one of the cell recovery outputs is connected to a subsequent sorting chamber. Thus the selective output of the first unit is connected to the input of a second unit where further sorting takes place. This manner of cascading allows the technician to be increasingly selective about the types of cells sorted.

An optical cell stream detector is provided at a strategic point along the sorting system to permit adjustments in the cell spread via the adjusting fluid intake flow rate controls and by varying field strengths and frequencies.

Other objects and details of the present invention will become apparent from the following detailed description.

BRIEF DESCRIPTION OF THE DRAWINGS

The present invention will be more fully understood by reference to the following detailed description of the preferred embodiments of the present invention when read in conjunction with the accompanying drawings, in which like reference characters refer to like parts throughout the views, and in which:

FIG. 6 is an elevated side view shown in partial cross-section and illustrating interconnected stacked sorting chambers according to the present invention.

DETAILED DESCRIPTION OF THE PREFERRED EMBODIMENTS OF THE PRESENT INVENTION

The drawings disclose the preferred embodiments of the present invention. While the configurations according to the illustrated embodiments are preferred, it is envisioned that alternate configurations of the present invention may be adopted without deviating from the invention as portrayed. The preferred embodiments are discussed hereafter.

Figure 1:
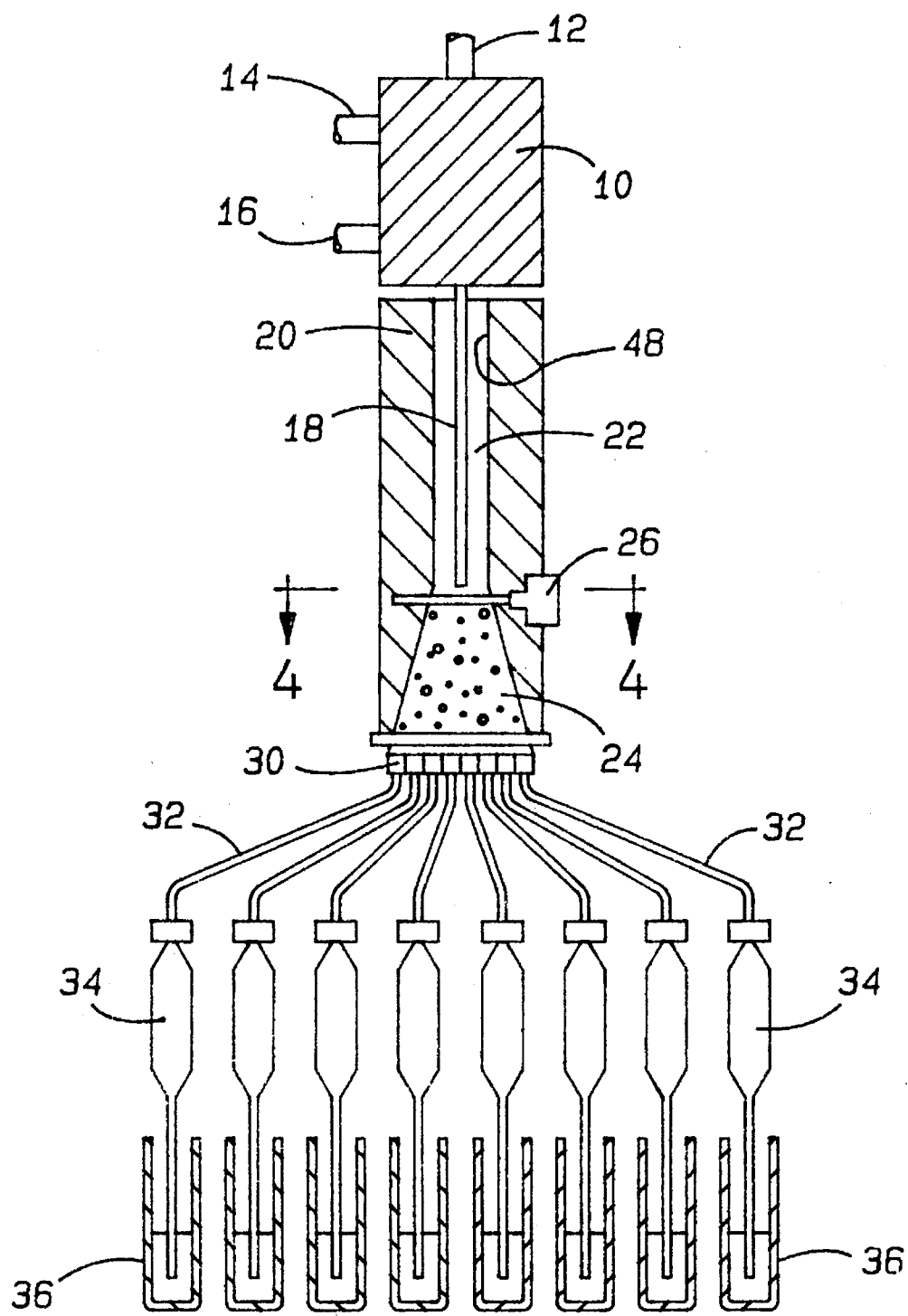
FIG. 1 is an elevated side view shown in partial cross-section and illustrating the overall system of the sorter of the present invention.

Referring to FIG. 1, an elevated side view of the present invention, shown in partial cross-section, is illustrated. This view illustrates the overall sorting system from cell intake to final collection.

The system of the present invention may be generally divided into four stages: the intake stage, the expansion (sorting) stage, the pumping stage, and the final collection stage.

The first stage, the intake stage is embodied in an intake chamber 10. The intake chamber 10 includes a cell intake port 12, a deionized buffered medium fluid intake port 14, and a "sheathing" deionized buffered fluid intake port 16. The cells in the fluids exit the cell intake chamber 10 through a coaxial outlet tube 18. The cell intake chamber 10 is more fully described below with respect to FIG. 2.

The outlet tube 18 extends beyond the chamber 10 into a deflection chamber 20. The deflection chamber 20 includes a non-tapered channel entrance 22. The deflection chamber 20 is illustrated and discussed in further detail below with respect to FIG. 2.

As the cells and their suspending fluids continue to be drawn through the deflection chamber 20 and into an expansion chamber 24, the stream of cells are fanned out. This chamber 24 is of a flared design to accommodate the fanning of the cells while allowing for an alteration of the flow rate and the field positions to remain relatively constant along the path of flow.

A strategically placed video camera 26 allows the operator to optically observe the cell spread and make the necessary adjustments to the intake fluid flow rates, field strength, and field frequency to maximize separation.

At the base of the expansion chamber 24 is an exit portal separation plate 30. The separation plate 30, preferably composed of a material such as Lexan (trademark belonging to General Electric Company for polycarbonate resin sheet material), has a series of tapered outlet holes (not shown). The outlet holes allow for the passage of sorted cells which are drawn without turbulence to the nearest outlet hole by a vacuum action through vacuum pumps (described below).

Once through separation plate 30, a series of sorted cell outlet lines 32 carry the now separated cells to a like number of vacuum pumps 34. The vacuum pumps 34 are a critical feature of the present invention in that by drawing the cells and their carrier fluids through the system, this method of moving the cells and their carrier fluids provides a smooth flow of the cells into the intended collection chambers. The pumps 34, because they are vacuum-type, draw the cells and the fluid through the system rather than forcing this material through by pressure, as is known in conventional systems that have pumps that push, rather than pull the fluid and the carried cells. This assumes, of course, that the cell intake port 12 and the cell fluid intake ports 14 and 16 are all well sealed and are properly fitted to their appropriate reservoirs (not shown), thereby preventing any chance input of ambient air into the system.

An advantage of the draw system of the present invention is the elimination of turbulence. This is essential at those points where the moving fluid and suspended cells leave the expansion chamber 24 and pass through the plate 30. This approach overcomes the turbulence that is always at fluid dividing points. Pumped fluids always develop turbulence at the "doctor's knife" or the point of physical stream separation. The present system overcomes this problem.

After being drawn through the system and sorted in response to the RF fields, the sorted cells and their carrying fluid are deposited into a series of cell recovery reservoirs 36. Eight recovery reservoirs 36 are illustrated, as are eight associated gravity pumps 34 and eight lines 32. Although not illustrated, each or any recovery reservoir 36 may have a line leading to the cell intake end of another sorting unit for additional sorting of the material. Accordingly, the RF generators of the first system may be adjusted to sort a given mixture of cells only generally. The preliminarily sorted cells can then be resorted according to the setting of a second unit to further differentiate between cells. This cascading approach allows the technician to be increasingly selective about the population of cells recovered through continuous repetitive sorting. The only limitation on the number of tiers of resorting is the time in the buffered solution. For high viability, the total time out of growing medium is generally limited to twenty minutes. There is almost no limit on the number of outlet reservoirs per tier. The gravity pump system requires that the exit portals have a greater total volumetric capacity than the total volume of the combined intakes.

Figure 2:
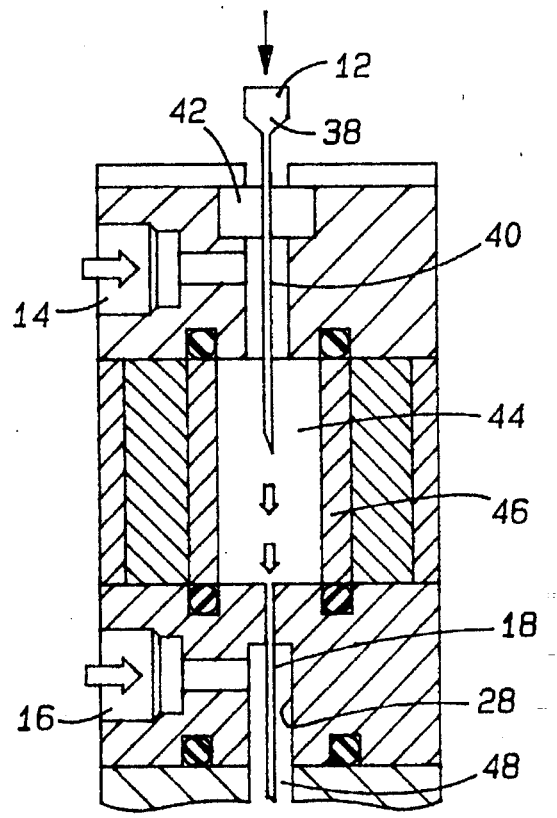
FIG. 2 is a detailed view of the two-staged cell transporter shown in cross-section.

FIG. 2 is a detailed view of the cell intake chamber 10 of the present invention shown in cross-section. This system is two-staged because it first introduces a buffered cell medium fluid with the cells in growing medium and then a sheathing carrier fluid, introduced at a second lower stage.

The cell intake port 12 includes a cell in growing medium reservoir and receiving tube 38 attached to the top of an intake needle 40. The intake needle 40 is fitted to the cell intake chamber 10 by pushing it through a rubber septum 42. The septum 42 provides a tight seal around the needle 40 thereby preventing air, foreign material, or any microorganisms from contaminating the system.

The end of the intake needle 40 terminates within a first chamber 44. The cells enter the first chamber 44 through needle 40. The first chamber 44 is fluidly interconnected with the deionized, buffered cell medium intake port 14. A buffered deionized solution enters the chamber 44 through the intake port 14. The cell suspension is now composed of the cells to be sorted in a concentrated highly deionized solution. (All fluids used in the system of the present invention are deionized so that the RF field electronically "sees" the cells and not the fluids.)

Within chamber 44, the cells, now in the buffered deionized solution, await processing. The cell medium is a buffered solution to prevent the cells from rupturing while awaiting movement through the outlet 18 and into a receiving neck 48 of the deflection chamber 20. The receiving neck 48 of the deflection chamber 20 is continuous with a sheathing fluid output port 28.

A continuous wall 46 composed of a material such as Pyrex (trademark belonging to Corning, Incorporated for borosilicate glass) is provided to surround the chamber 44.

Concurrent with the passage of the cell suspension solution into the deflection chamber 20, is the introduction of a buffered deionized sheathing fluid through the fluid input port 16 and out of the output port 28 into the neck 48. The sheathing fluid is introduced into the deflection chamber 20 at such a rate that the cell solution stream exiting the outlet tube 18 remains centered in the sheathing stream so that the cell solution is sheathed by the sheathing stream as the solution proceeds through the channel entrance 22 and into the expansion chamber 24.

Figure 3:
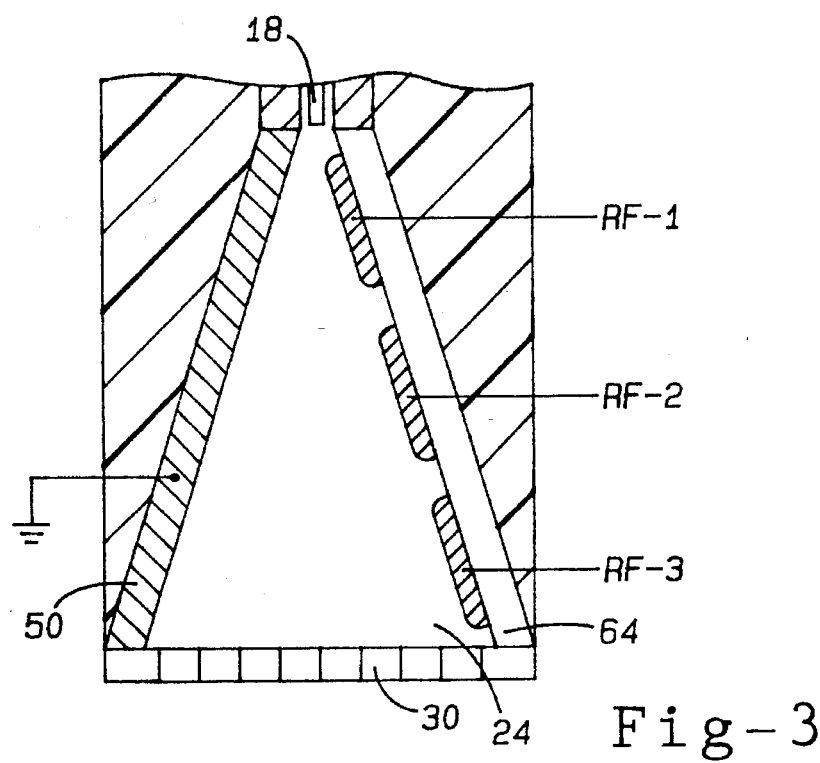
FIG. 3 is a detailed view of the deflection chamber.

FIG. 3 illustrates a detailed view of the expansion chamber 24. This view is particularly valuable in that it illustrates the series of electrodes of the RF field generator.

As illustrated, one side of the expansion chamber 24 comprises a ground plate 50. The plate 50 preferably is composed of a chrome-plated brass plate. Opposite the plate 50 is a wall 64. The wall 64 is preferably composed of Lexan (trademark belonging to General Electric Company for polycarbonate resin sheet material). A first RF field electrode denoted "RF-1" is provided on the chamber-side of the wall 64. An additional series of RF field electrodes are provided in succession down the same side of the chamber 24, and include RF-2 and RF-3. A greater or lesser number of such electrodes may be used as necessary according to the sorting undertaken. The electrodes are preferably composed of platinum, although it is conceivable that other materials of high electrical conductivity may be used.

Cells respond differently to different RF frequencies. By adjusting such variables as the strength of the RF signal and its frequency, the subject cells can be fanned out and "directed" to particular apertures in separation plate 30 as they exit deflection chamber 20. This may be better understood by reference to FIG. 5, below. In addition, the spacing of the electrodes labeled RF-1 through RF-3 (more or less may be provided) can also be modified to thereby have a particular cell respond in a particular way, either moving toward or away from the electrodes, or toward or away from a given aperture in separation plate 30. By adjusting the frequency, signal strength, and varying the electrodes used, sorting can be accomplished with considerable definiteness and differentiation.

Figure 4:
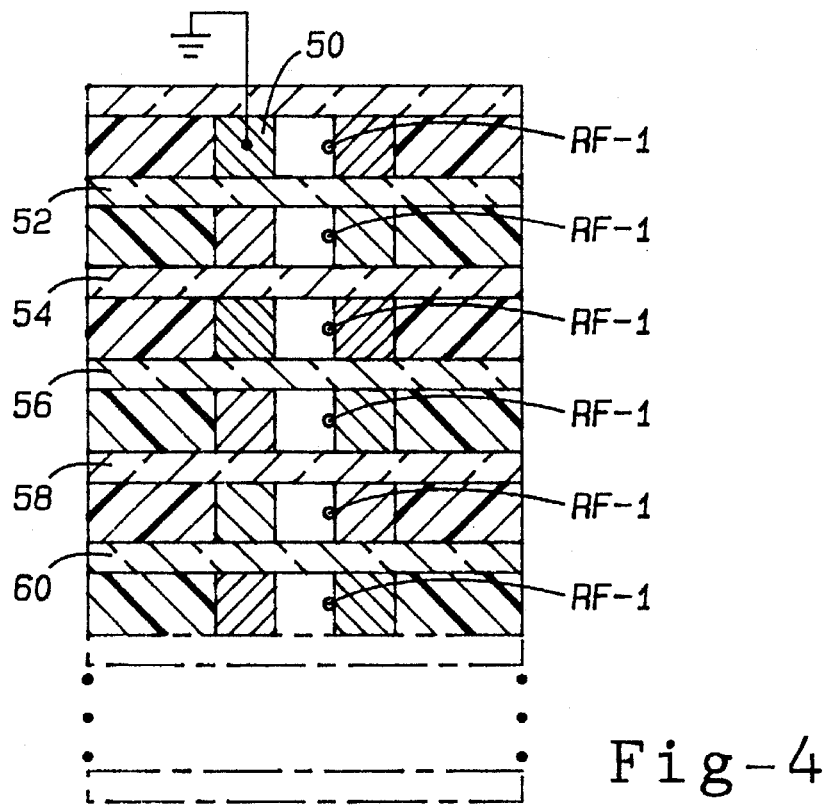
FIG. 4 is a view detailing an optional, multi layered stacked chamber.

FIG. 4 illustrates an optional, multiple-layered arrangement. The "stacked chamber" illustrated here provides a system of multiple, side-by-side deflection chambers. This construction allows the operator to sort an even larger quantity of the same cell batch under like conditions in the given time frame using the same frequency generators and settings. A plurality of separating walls 52, 54, 56, 58, 60, and so forth, run the full length of the deflection chambers. Individual cell and separate pumps and output reservoirs are used. The intakes are all supplied from the same reservoirs (not shown).

Figure 5:
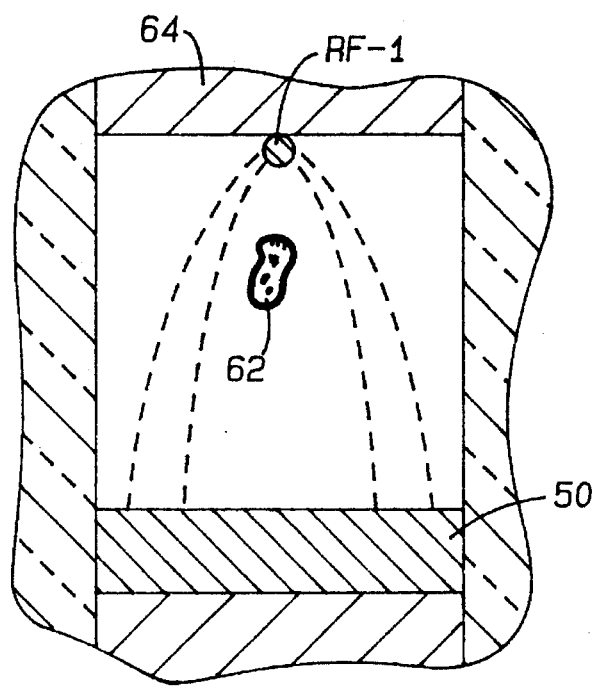
FIG. 5 is a detailed view of a chamber illustrating the effect of an RF field upon an individual cell.

FIG. 5 illustrates a top detailed view of a chamber particularly illustrating the effect of an RF field upon an individual cell, indicated as 62. As illustrated, the RF-1 electrode sets up a field indicated in broken lines between the electrode and the ground plate 50. By way of example, with the electrode RF-1 being positive and the ground plate 50 being negative, the internal negative ions of the cell 62 migrate to one end opposite the electrode as the internal positive ions of the cell 62 migrate to the other end opposite the ground plate 50. By adjusting the frequency and strength of the RF field, the cell 62 can be selectively manipulated toward or away from the RF-1 electrode. Of course, the remaining electrodes in the series (shown in FIG. 3) can be adjusted to further manipulate the cell 62.

FIG. 6 is an elevated side view shown in partial cross-section and illustrating interconnected stacked sorting chambers according to the present invention. A master chamber 66 is illustrated having a plurality of cell distribution lines 68, 70, 72, 74 exiting therefrom. The cell distribution line 68 delivers sorted cells to a subsequent sorting chamber 76, while the cell distribution line 70 delivers sorted cells to a subsequent sorting chamber 78. Similarly, the cell distribution line 72 delivers sorted cells to a subsequent sorting chamber 80, while the cell distribution line 74 delivers sorted cells to a subsequent sorting chamber 82.

Having described my invention, however, many modifications thereto will become apparent to those skilled in the art to which it pertains without deviation from the spirit of the invention as defined by the scope of the appended claims.

I claim:

1. A method for continuously sorting selected cells from a heterogenous mixture of cells to obtain separate populations, said method comprising the steps of:

transporting living cells in a growing medium fluid into the entry port of a cell sorting apparatus;

mixing said cells into a suitable processing medium fluid to create a cell suspension;

transporting said cell suspension into an expansion chamber;

exposing said cell suspension contained within said expansion chamber to a radio frequency field to cause said living cells to move in response to said radio frequency field to different collection regions of said chamber to be separately collected; and adjusting said radio frequency field in both frequency and strength to maximize desired sorting;

said cell suspension being vacuum drawn during said steps by a vacuum pump.

2. The method for continuously sorting living cells according to claim 1 further including the step of surrounding said cell suspension by a fluid sheath, said fluid sheath having a center, as said suspension enters said expansion chamber by holding said cell suspension in said center of said sheathing fluid.

3. The method for continuously sorting living cells according to claim 1 wherein said cell suspension is exposed to a series of radio frequency fields in sequence.

4. The method for continuously sorting living cells according to claim 1 including the additional step of depositing the sorted cells into cell recovery reservoirs after being drawn through said apparatus by said vacuum pump.

5. The method of continuously sorting living cells according to claim 1 wherein said cells sorted into said separate cell collection regions are resorted through repetition in subsequent interconnected sorting chambers.

6. The method of continuously sorting living cells according to claim 1 further including the step of subsequently sorting groups of sorted cells in a stacked expansion chambers.

\* \* \* \* \*